US007044926B2

(12) United States Patent
Carlson

(10) Patent No.: US 7,044,926 B2
(45) Date of Patent: May 16, 2006

(54) SPHERICAL JOINT ORTHOSIS

(75) Inventor: J. Martin Carlson, Mora, MN (US)

(73) Assignee: Tamarack Habilitation Technologies, Inc., Blaine, MN (US)

( * ) Notice: Subject to any disclaimer, the term of this patent is extended or adjusted under 35 U.S.C. 154(b) by 0 days.

(21) Appl. No.: 10/785,791

(22) Filed: Feb. 24, 2004

(65) Prior Publication Data

US 2005/0187505 A1 Aug. 25, 2005

(51) Int. Cl.
*A61F 5/00* (2006.01)

(52) U.S. Cl. .................. 602/27; 23/65; 23/16
(58) Field of Classification Search ............... 602/16, 602/5, 20, 21, 22, 23, 28–29, 62; 128/80 C
See application file for complete search history.

(56) References Cited

U.S. PATENT DOCUMENTS

| 2,645,365 | A | | 10/1953 | Whitaker | 128/80 |
|---|---|---|---|---|---|
| 3,532,371 | A | | 10/1970 | Ortheil | 287/88 |
| 3,799,158 | A | | 3/1974 | Gardner | 128/80 C |
| 4,136,404 | A | | 1/1979 | Lange | 2/22 |
| 4,174,137 | A | | 11/1979 | Ferris | 308/72 |
| 4,241,730 | A | | 12/1980 | Helfet | 128/80 C |
| 4,256,097 | A | | 3/1981 | Willis | 128/80 C |
| 4,520,804 | A | * | 6/1985 | DiGeorge | 602/16 |
| 4,576,151 | A | * | 3/1986 | Carmichael et al. | 602/24 |
| 4,603,690 | A | | 8/1986 | Skeen | 128/80 C |
| 4,620,532 | A | * | 11/1986 | Houswerth | 602/16 |
| 4,817,588 | A | * | 4/1989 | Bledsoe | 602/16 |
| 4,982,732 | A | * | 1/1991 | Morris | 602/16 |
| 5,000,169 | A | * | 3/1991 | Swicegood et al. | 602/16 |
| 5,400,806 | A | | 3/1995 | Taylor | 128/898 |
| 5,409,449 | A | * | 4/1995 | Nebolon | 602/16 |
| 5,460,599 | A | * | 10/1995 | Davis et al. | 602/26 |
| 5,611,773 | A | * | 3/1997 | Nash et al. | 602/16 |
| 5,800,370 | A | | 9/1998 | Kubein-Meesenburg et al. | 602/26 |
| 5,814,000 | A | * | 9/1998 | Kilbey | 602/16 |
| 5,826,304 | A | | 10/1998 | Carlson | 16/225 |
| 5,997,493 | A | * | 12/1999 | Young | 602/16 |
| 6,045,524 | A | * | 4/2000 | Hayashi et al. | 602/23 |
| 6,090,057 | A | | 7/2000 | Collins et al. | 602/16 |

(Continued)

FOREIGN PATENT DOCUMENTS

DE 199 28 269 A1 6/1999

(Continued)

OTHER PUBLICATIONS

Fillaver, Inc., "Universal Ankle Joint Fabrication Instructions" and illustrations (4 sheets), published Dec. 2001.

(Continued)

*Primary Examiner*—Henry Bennett
*Assistant Examiner*—Shumaya B. Ali
(74) *Attorney, Agent, or Firm*—Westman, Champlin & Kelly, P.A.

(57) ABSTRACT

An orthosis that provides hinging action between two shell parts that are on opposite sides of a skeletal joint of a limb is provided with joint components on the medial and lateral sides of the skeletal joint. A spherical bearing connection between two parts of each of the joint components is used. The spherical connection is such that the pivot axes of the medial and lateral joint component do not have to be precisely coaxial when hinging due to the accommodation by the spherical bearing. Also, in fabricating an orthosis, a dummy joint component is used in the molding process, or, for metal frame fabrication and repair, the joint is plugged in neutral alignment during the fabrication process.

10 Claims, 9 Drawing Sheets

U.S. PATENT DOCUMENTS 6,142,964 A * 11/2000 Gilmour ........................ 602/20
6,740,054 B1 * 5/2004 Stearns ........................ 602/16

FOREIGN PATENT DOCUMENTS

GB             1534434      9/1977
WO     WO 93/20782    10/1993

OTHER PUBLICATIONS

United States Manufacturing Company instructions and illustration of "COD Self-Aligning Ankle Joints" (2 sheets), published at least as early as Aug. 1, 2000.

Copy of Search Report under Section 17(5).

* cited by examiner

SPHERICAL JOINT ORTHOSIS

BACKGROUND OF THE INVENTION

The present invention relates to spherical hinges for hinging portions of an orthotic shell or brace that is used to stabilize a body anatomical joint. As shown, a foot support portion and a leg shell portion are hinged together. The spherical hinge accommodates some misalignment of hinge axes on opposite sides of a human limb joint so the assembly of two portions to obtain a freely movable orthosis is much easier.

The leg and foot shell portions of an ankle orthosis have long been hinged together with simple, single axis, pinned lap joint type hinges or with flexure units, such as that shown in U.S. Pat. No. 5,826,304. The flexure unit fills a distinct purpose, but in certain instances, it is orthopedically desirable to have a way to adjust the angle at which free ankle motion is stopped. This may be advantageous to accommodate changes in a patient's condition or to search out the orthotic control conditions which optimize gait.

Orthopedic braces are typically custom fabricated, one at a time by hand. In such fabrication circumstances, the ability to mount the hinges without precise alignment, and without increasing binding, stress, and conditions that cause a lot of wear, means that the finished orthosis can be fabricated at a considerably lower labor cost. Also, the ankle joints not only will function better but will last longer.

It is often the case that people who have orthopedic impairments involving one or more of the limbs can be aided by an orthosis (orthopedic brace). When an orthosis crosses a skeletal joint, for instance the ankle, as shown herein, or the knee, wrist, or elbow, there is usually a need to incorporate a set of hinge components (one on each side of the limb) into the structure of the orthosis.

When the orthosis must provide significant stabilization, deformity correcting, moments to the limb, the orthosis includes hinging components on both the medial and lateral aspects of the orthosis structure. The medial and lateral aspects of the orthosis structure desirably must pivot on an axis in line with each other and the axis of the anatomical joint in order to be comfortable, safe and cosmetic as well as provide orthopedic support.

Most limb orthosis are custom fabricated and fit to the individual user. The choice and proper incorporation of hinging components is an important aspect of that custom design and manual fabrication process. The orthotic industry does make use of some flexure type components that automatically achieve neutral axis alignment or co-alignment, because of the design. However, the flexure joints do not include an intrinsic, adjustable motion stop, which is sometimes needed. An example of such a device is shown in the previously mentioned U.S. Pat. No. 5,826,304.

Substantially all non-flexure joint components are of a pinned lap or clevis type, constrained by close tolerances to pivot about a single axis or a predetermined series of parallel axes. The pivoting parts "bind" if the medial joint component is not accurately co-aligned with the lateral joint component. In other words, the joint components on opposite sides of the actual skeletal or anatomical joint being supported must align. "Binding" due to misalignment causes higher rates of wear in the orthotic joints and hastens failure, and such binding from inadequate co-alignment can also cause distortion and extra stresses on other parts of the orthosis structure thus will produce unintended extra loads and constraints on the user's anatomy.

Those and other reasons result in the need for a great deal of care, as well as a great deal of time for fabrication to ensure co-alignment of the medial and lateral hinge or joint components. Orthotic design in recent years has resulted in considerable use of plastic shell-type structures, which are lighter and can be made to fit better. However, the plastic shells flex and bend as they come under bearing loads during use in ways that can cause joints to bind, even if the original co-alignment was perfect. In other words, in use, the joints built into plastic shell-type structures can change positions and alignment during gait.

Precise co-alignment of ankle and knee joints usually requires the use of special fixtures during fabrication. The fixtures bolt onto the joints to hold the medial and lateral joint or hinge components so that their axes of rotation coincide (co-alignment) throughout the fabrication process, to the completion of the process. The fabrication process involves hand bending and shaping of medial and lateral longitudinal bars that extend upward and downward from the joints. The bars are contoured to follow a unique pattern or plaster mold of a patient's leg. Those bars must be attached firmly to metal and/or plastic structural components, such as calf bands, thigh bands, and/or the plastic shells above and below the joint. To accomplish all that bending, shaping, and rigid structural integration, while at the same time maintaining joint co-alignment of the joint heads or components requires immense skill, care, and time. Compromises are made, which sacrifice precision of co-alignment or close fit.

Some orthoses incorporating knee joints have an additional co-alignment challenge. Bale type knee joint components incorporate a rigid semi-circular posterior linkage or bale, between the medial and lateral joint locking mechanisms. These locking mechanisms can be cams or tooth-type locks for locking the joint. This locking is to ensure there will not be any unwanted movement, or release of the joint at an inappropriate time. It is clear that the medial and lateral joint components then should lock and unlock in unison. Binding caused by inadequate co-alignment and/or by structural flexing will then also lead to wear, failure, and unreliable function of a walk enabling mechanism. Orthoses that incorporate a rigid bale lock also benefit from the present invention forming means for hinging the bale.

Co-alignment requirements also complicate the work of the orthotic technician when the orthosis must be repaired or modified, as may be necessary to accommodate changes in the patient's weight or orthopedic conditions. It should be noted that the Motloch-Fillauer ankle joint sold by Fillauer, Inc. of Chattanooga, Tenn., U.S.A. provides ankle joint pairs in a fabrication kit that includes attachment rod end spherical joints, but these joints have a problem with loads that are incurred because of the mountings. Also, they do not incorporate a means to limit/stop motion.

SUMMARY OF THE INVENTION

The present invention relates to hinge components for orthoses that are associated with an anatomical skeletal joint. The hinge components use a spherical bearing at the hinge axis to permit ease of mounting while still obtaining precise operation.

The present hinge component accommodates some offset or misalignment of the hinge components on opposite sides of the skeletal joint without binding or creating an unwanted load on the spherical bearing utilized in the hinge of the joint components. The hinge components also include an integral, adjustable motion stop. In accordance with the present invention, the mounting of the medial and lateral joint components in orthosis parts is greatly simplified.

The orthotic joint design of the present invention is a combination of a clevis on a first part of the joint component and a spherical bearing on the second part. The design allows the pivot axis between the two parts to freely lie anywhere within a conical region accommodated by the ability of the two parts to tilt on a part spherical bearing from a centered portion. In the present invention, for example, tilt motion can vary in any direction within the limits of a 24° cone. The ball joint or spherical bearing permits free rotation of the two parts about the pivot axis anywhere in this conical region. The spherical bearing eliminates binding of the medial and lateral joints unless alignment discrepancies from fabrication or structural flexing exceed the 24° range of accommodation. Since the potential axis location region is conical, again in the plus or minus 12° range of tilt in any plane from the neutral axis, alignment discrepancies in any of the planes on axis in a cone up to 24°, are accommodated.

Thus, it is a quick and easy matter to align by various approximate visual methods the medial and lateral joint components to within that range of plus or minus 12° of each other. The clevis on one joint component part attached by means of a through pin to the spherical bearing on the other part therefore saves fabrication time as well as avoiding accelerated joint wear and operational failure.

Also, in fabrication, the clevis end of the one joint part of the present invention can have a plug that takes up the space within the clevis flanges so that the axis of rotation established by the clevis pin cannot vary from its middle or neutral location during fabrication procedures. The technician doing the fabrication will need to co-align the joints to within some reasonable limit, which in the example described, is plus or minus 12°. This will keep them in their neutral or mid-alignment during fabrication and will be helpful to avoid the spherical bearing from being at or near the limits of the joint co-alignment capability when fabrication of the device is complete. The plug may be made of sheet metal or may be plastic.

In addition, the shell that is used for the orthosis can have a rigid or non-functional dummy of the joint in place during fabrication of the two hinged parts of the orthosis shell. The dummy is a rigid metal or plastic version of the joint without the spherical component, and fixed in neutral or mid alignment. It will simply create appropriate cavities in the custom molding of plastic shell parts that will receive the actual pivoting or articulating joint components near the end of the fabrication process.

It is also noted that artificial knee joints are used in connection with thigh corsets on some prosthesis made for people with trans-tibial amputations. For those and other circumstances, the present joint technology is useful in prosthesis fabrication as well.

DETAILED DESCRIPTION OF THE PREFERRED EMBODIMENTS

Figure 1:
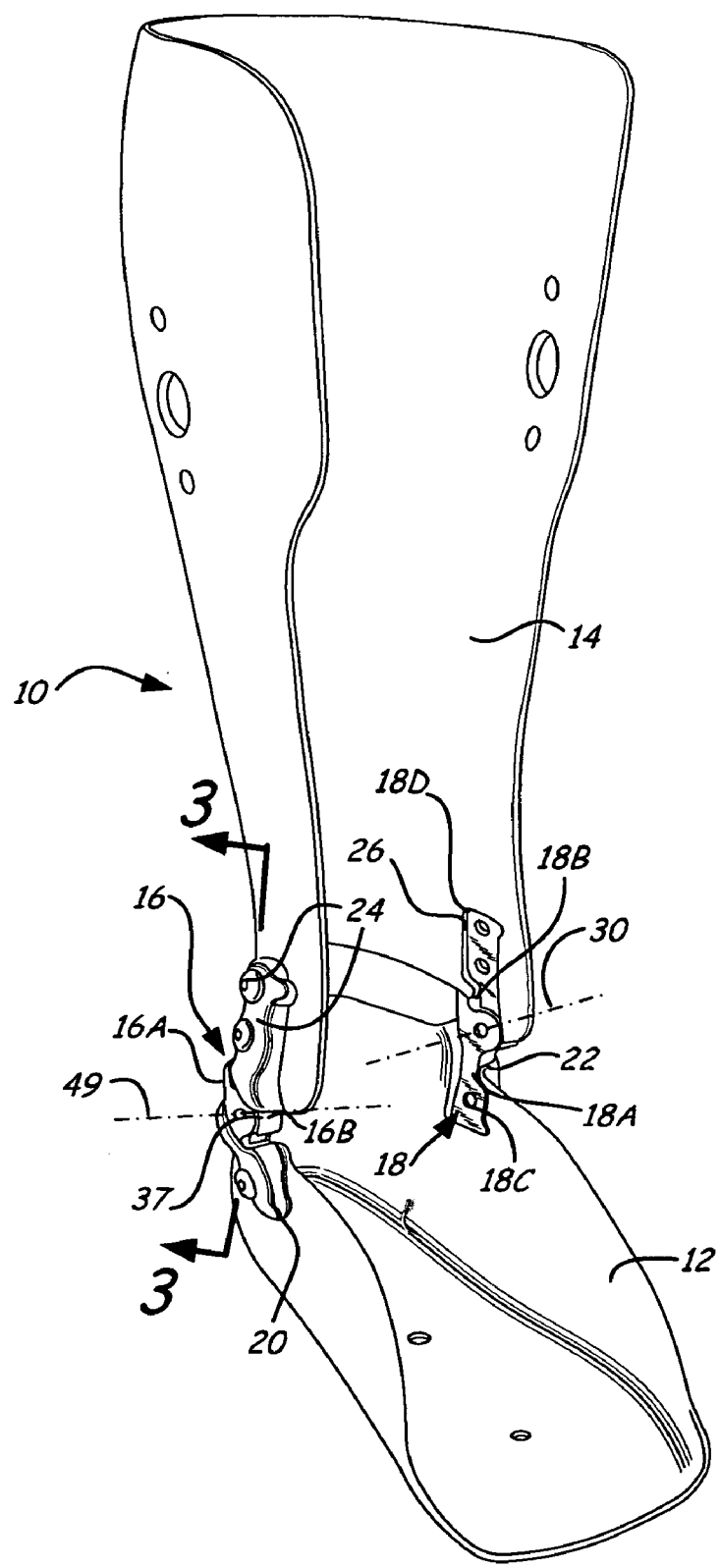
FIG. 1 is a perspective view of an orthosis comprising an ankle joint, having hinge components made according to the present invention.
Figure 2:
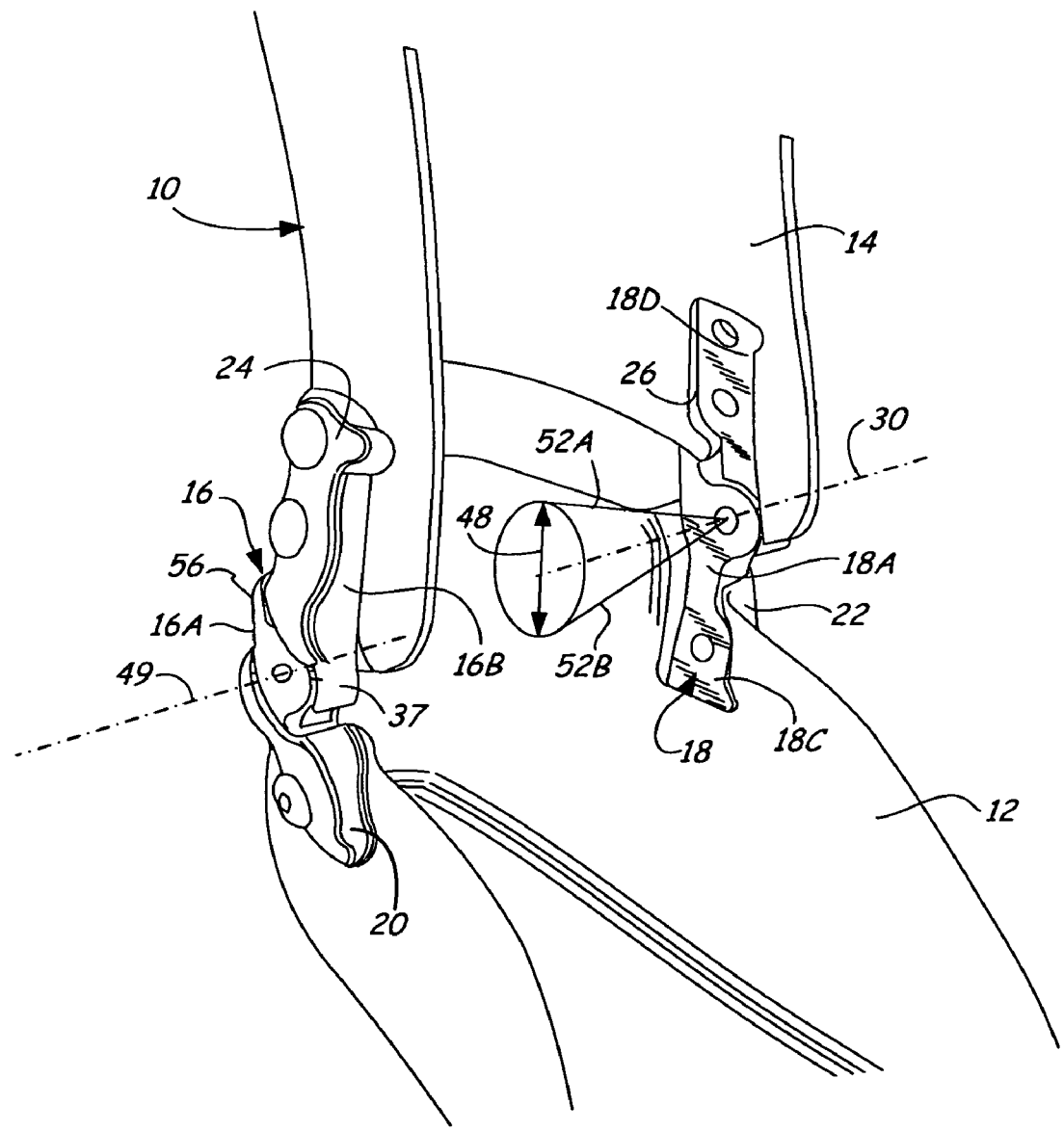
FIG. 2 is a fragmentary enlarged view of the joint components of FIG. 1.

Referring to FIG. 1, an orthosis indicated generally at 10 in this form of the invention is for use in connection with an ankle joint, and includes a foot section 12, and a lower leg section 14. The foot section and leg section 14 are held together with a pair of ankle joint components shown at 16 and 18, respectively. The ankle joint component 16 is the lateral ankle joint component and the ankle joint 18 component is the medial ankle joint component. The ankle joint components in this form of the invention are hinges that are provided in pairs one on each side of the skeletal or an anatomical ankle joint of a wearer of the orthosis. The joint components 16 and 18 comprise two pivotally connected parts. The clevis part or section 16A and 18A, respectively, are mounted on the respective sides of the foot section 12, and the upper or leg parts 16B and 18B carry a part spherical bearing and are mounted on the leg section. The respective foot section joint component parts 16A and 16B have support straps 16C and 18C, respectively, secured to the foot section 12, which are fitted into molded pockets 20 and 22 on the lateral and medial sides of the foot section, as shown.

The upper or leg section parts 16B and 18B of the joint components have support straps 16D and 18D, respectively, that are molded into pockets 24 and 26 on the lateral and medial sides, respectively, of the leg section 14. These straps are suitably secured in place with rivets or screws, or in other ways, to hold the two parts of each joint component so they pivot along a generally transverse axis indicated at 30, that would represent the axis of motion of a foot in the foot section 12 relative to a lower leg in the leg section 14.

Figure 3:
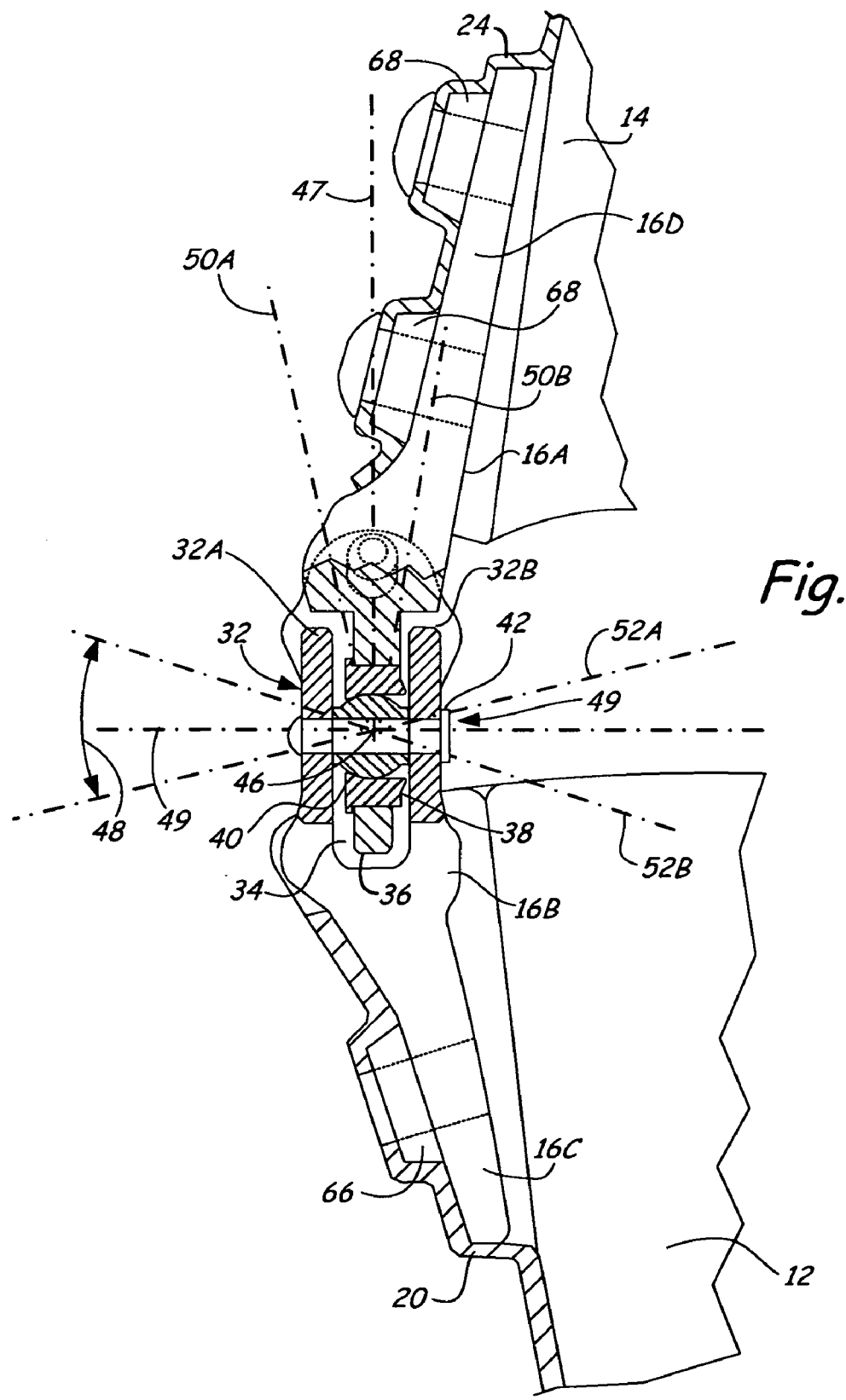
FIG. 3 is a sectional view taken as one line 3—3 in FIG. 1.

The clevis carrying parts or sections 16A and 18A are mirror images and constructed the same. The description in connection with FIG. 3 explains joint component 16, but joint component 18 is made in the same way. Each clevis 32 is at the upper end of the respective foot section part and has two separated flanges 32A and 32B, on the lateral and medial sides, respectively. The flanges 32A and 32B are spaced apart to form a receptacle 34 that receives a tongue 36 forming an extension from the upper straps 16D or 18D, of the leg section parts 16A and 18A, as shown in FIG. 3, the strap 16D.

Figure 4:
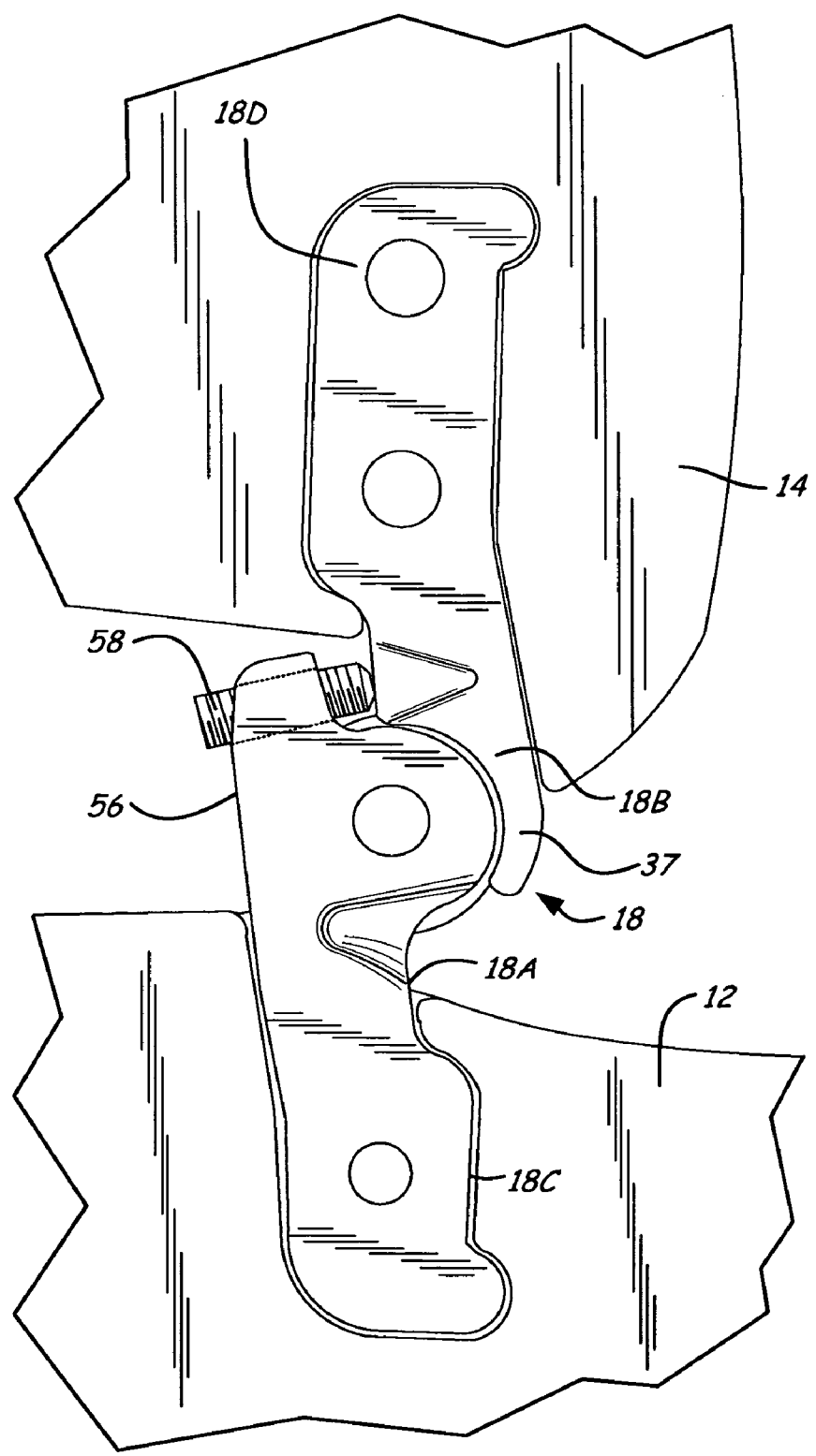
FIG. 4 is a fragmentary side view of showing an ankle joint component with an adjustable stop screw in position.
Figure 5:
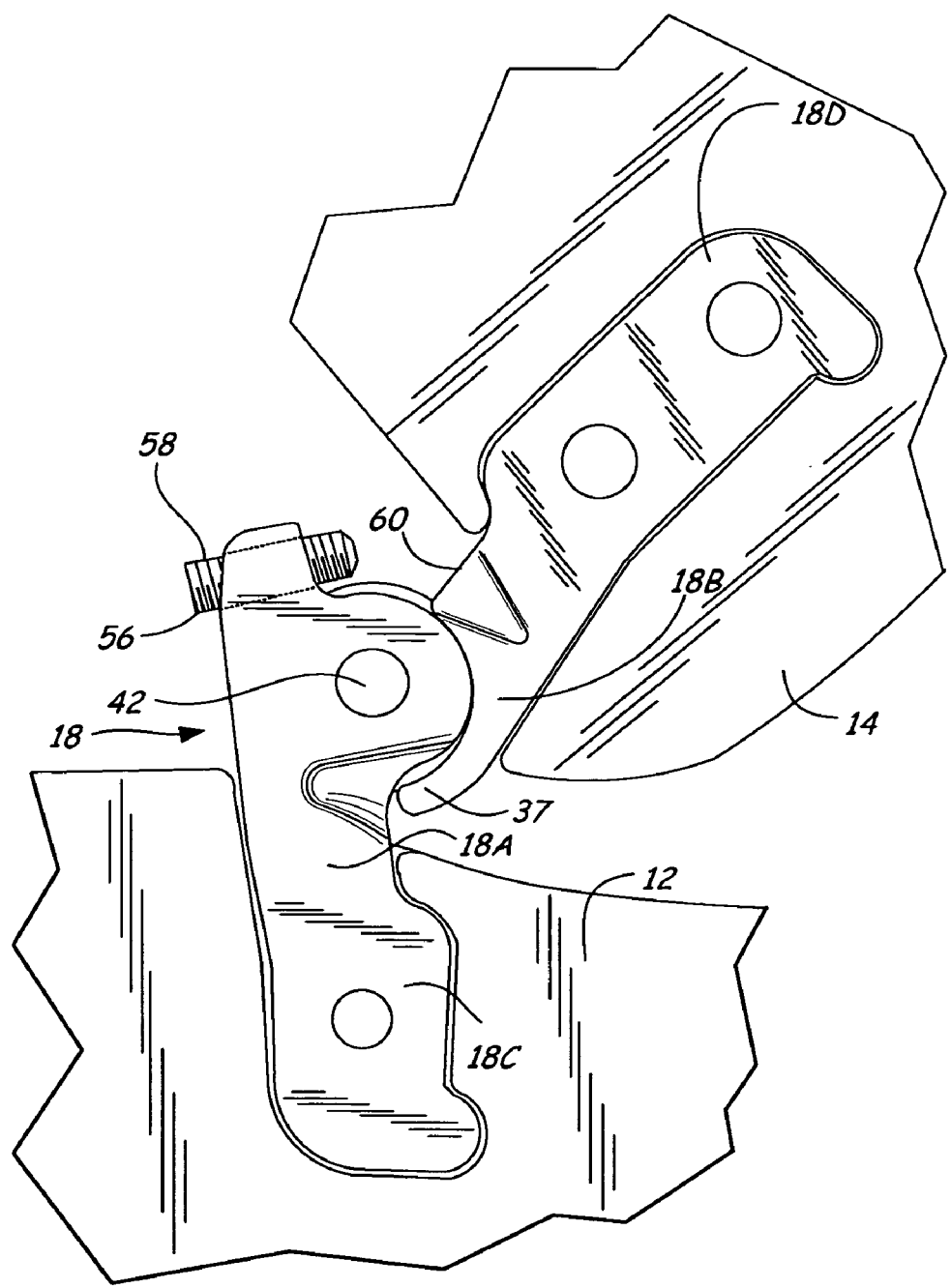
FIG. 5 is a view similar to FIG. 4 with the orthosis sections provided.

The tongue 36 has a spherical bearing race 38 supported therein, and the bearing race 38 holds a spherical outer surface bearing 40. The spherical bearing 40 is universally pivotable in the race 38, and has a central bore through which a rivet or suitable fastener 42 can be passed to secure the two hinge parts of each joint component together for pivoting or hinging the upper part or section 16B and 18B of the joint component to the respective clevis 32. As can be seen in FIGS. 4 and 5, the upper part 18B and 16B have a flange 37 that overlies the clevis and tongue to shield the pivot. The flange 37 spans the two flanges 32A and 32B. The medial and lateral hinge components 16 and 18 again are mirror images of each other, so only one is described.

As can be seen, the tongue 36 is recessed in from the outer side edges of the upper support strap 16D. As indicated by double arrow 48 in FIG. 3, the part spherical bearing 40 will permit limited angular motion about a fore and aft axis 46 perpendicular to the central axis 49 of the rivet or pin 42 from a centered position. This is shown in the range of plus or minus 12° from a central plane 47 that lies along axis 46 and that is perpendicular to the axis of the pin 42. Lines 50A and 50B in FIG. 3 represent the permissible medio-lateral angular movement of the two parts of the ankle joint components. This would provide for a total movement of approximately 24° about fore and aft axis 46, in a typical example, and this in turn would provide for the same movement relative to the central axis 48, as represented at lines 52A and 52B.

The feature of a part spherical joint, such as that using the part spherical bearing 40, is that it will hinge or move freely about any axis lying within the 24° cone set. Both joint components will rotate freely when the two parts of the respective joint component are at any angular position about fore and aft axis 46 between the extreme limits shown at 52A and 52B.

The part spherical bearing 40 is preferably mounted in a self-lubricating race. One example of such a race is one that has voids in which the lubricant can be impregnated to limit wear. A sintered metal material impregnated with lubricant will work. PTFE impregnation will also work. The bearing race 38 is selected to provide for endurance and long life.

Because each of the ankle joint components 16 and 18 can operate freely on the spherical bearings or spherical connections within the conical range of movement illustrated by the lines 48, 52A and 52B, the axial alignment of the hinging or pivoting joint components on opposite sides of the skeletal joint being supported, such as the ankle, does not have to be perfect. In other words, the axis 49 of the pins 42 on the lateral and medial sides does not have to be perfectly coaxial. For example, as shown, if the axis 49 of the pin 42 on the medial side is above or below the axis 49 of the pin 42 on the lateral side, or if the axis is slightly tilted, relative to the skeletal or anatomical axis of the ankle movement, as long as the pin center of the medial joint falls within the conical axis range defined for the lateral joint, and vice versa, the pivot joints of the joint components will work freely and without binding or loading the actual ankle in the orthosis. Joint movement in each joint consists of a combination of rotation about the pin centerline and some rotation of the spherical member or ball around transverse axes.

Additionally, the present ankle joint components include an arrangement to stop the pivotal movement of the joint that would result in excessive downward movement of the toe of the foot supported in the foot section 12. In FIG. 4, for example, the front component 16 is shown. The part 16B has an integral housing 56 at an upper end, spaced from clevis 32 and from the axis 49 of the pivot rivet or pin 42. A set screw 58 is threadably mounted through a threaded bore in this housing 56, and will bear against a surface 60 on the upper part 16A of the joint. The same arrangement is present on the medial joint component 18A. By adjusting the set screw 58, the angular stop position of the joint component parts 16A and 16B when the front end of the stirrup 12 tends to drop, can be adjusted to fit the needs of the user of the orthosis.

The fabrication of the orthosis, using the joint components 16 and 18 of the present invention requires less alignment precision than is required when fabricating with adjustable stop joints of the prior art.

However, to ensure that the two pivoting parts of each of the joint components will be properly positioned in the recesses 20 and 22 formed in the foot section 12, and the recesses 24 and 26 in the leg section 14 for holding the parts of the joint components, a joint component dummy can be held in place during molding.

Some othoses for supporting and controlling the lower leg, ankle and foot are of metal frame construction. In such cases the problems associated with alignment during custom fabrication and with accelerated wear due to binding are much greater because the structure is more rigid. A joint component of the present invention designed for such applications would be very similar to what is described for plastic shell construction, but the flanges by which structural connection is made would be altered.

As noted earlier, orthoses which cross and control the knee as well as the ankle-foot complex, especially those utilizing bale locks require extraordinary attention to avoiding misalignment problems. Metal frame orthoses also require very different fabrication procedures. For such orthoses it is more practical to use a metal or plastic "plug" during fabrication to fill the clevis spaces and keep the joints restricted to a neutral or mid-alignment position during bending, grinding, welding, riveting, polishing, and similar necessary steps in fabrication.

Figure 6:
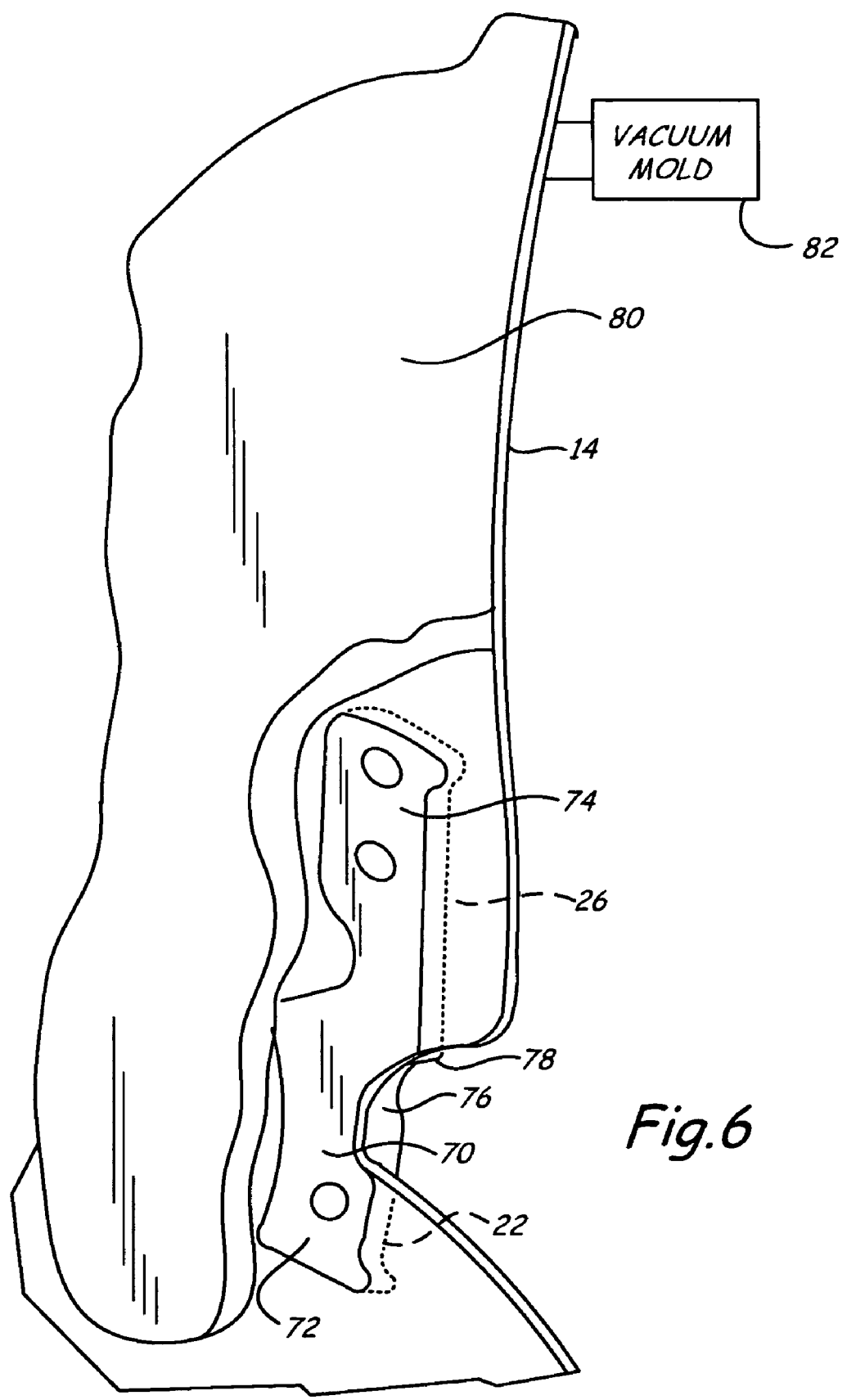
FIG. 6 is a fragmentary perspective view showing a rigid dummy joint component in place for holding the shell sections during molding and fabrication.

A dummy joint component shown in FIG. 6 at 70 replicates the mid-alignment configuration of the hinging joint component straps, namely the upper and lower straps of the hinged parts shown at 72 and 74. The dummy 70, and a mirror image dummy on the other side of the shell parts are in place while the recesses 20, 22, 24, 26 for the hinge parts are being formed or molded from plastic. The foot and the leg sections can be separated along edge lines 76 and 78 after molding, and then trimmed. The recesses are formed around the dummies, and the dummies 70 have protuberances that replicate the protuberances 66 and 68 (see FIG. 3) on the hinge parts that surround the bores for attachment screws. When molding, the receptacles are formed around the protuberances on the dummies so the receptacles are precisely located to guide the parts of the joint components into place. These receptacles locate the apertures for the screws on the hinge parts for accuracy in later mounting the actual joint components. The dummies must be rigid, as shown, because they represent mid-alignment configuration.

Additionally, the clevis end 32 can be supported with a plug that maintains the spacing between the clevis flanges 32A and 32B while the parts are being fabricated, so that the joint will not be at or near the limits of joint co-alignment capability before joint motion begins to take place during use.

Each molding dummy 70 is in a mid-range alignment configuration. The dummies 70 can be placed on the outside of a plaster cast shown at 80 that is made to simulate the leg of the person that will receive the orthosis, and using a vacuum mold 82, the plastic shell is molded around the plaster cart and the dummy hinges. The plastic is pre-heated and draped over the mold and will be sucked tight around the cast, and the hinge part dummies 70. Thus the recesses 20, 22, 24, and 26 will take the configuration of the dummy including the recesses that are formed by protuberances on the dummy where the protuberances 66 and 68 are positioned for the fastening screws, rivets or other fasteners would secure the actual joint component to the respective parts of the orthosis.

Figure 7:
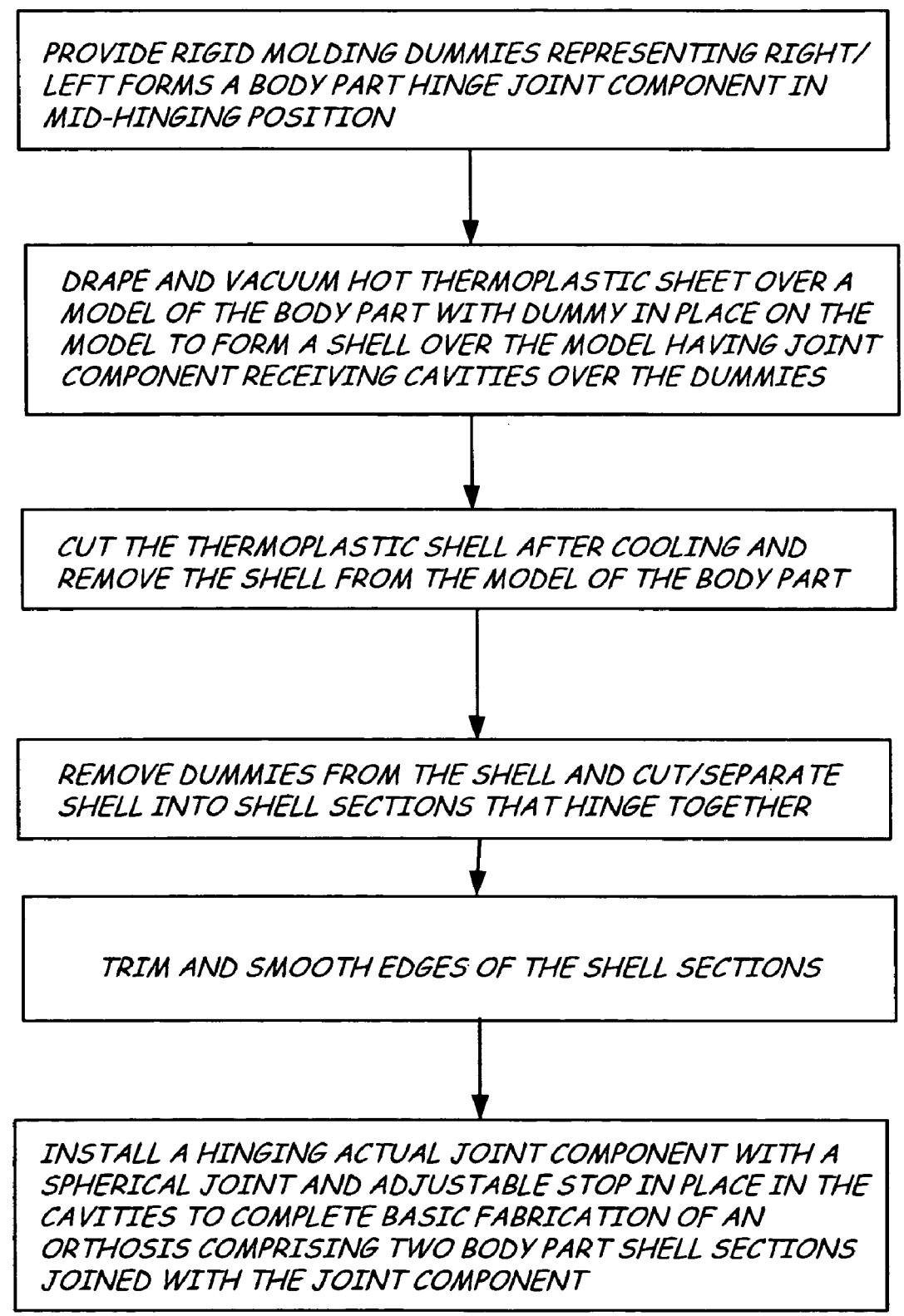
FIG. 7 is a flow chart showing a process for making a molded shell orthosis.

FIG. 7 represents a process flow chart with the steps of the process set forth in a normal sequence.

It also should be noted that the joint components may each have two adjustable stops, although only a single stop using one housing 56 is illustrated in the drawing. The second stop could be made by merely extending one or the other of the parts to form a housing similar to the housing 56, and a set screw would operate to stop pivoting in the opposite direction. Further, as stated, the two joint components can have hinge locks adjusted to lock in a particular angular position if needed for proper operation of the orthosis.

Figure 8:
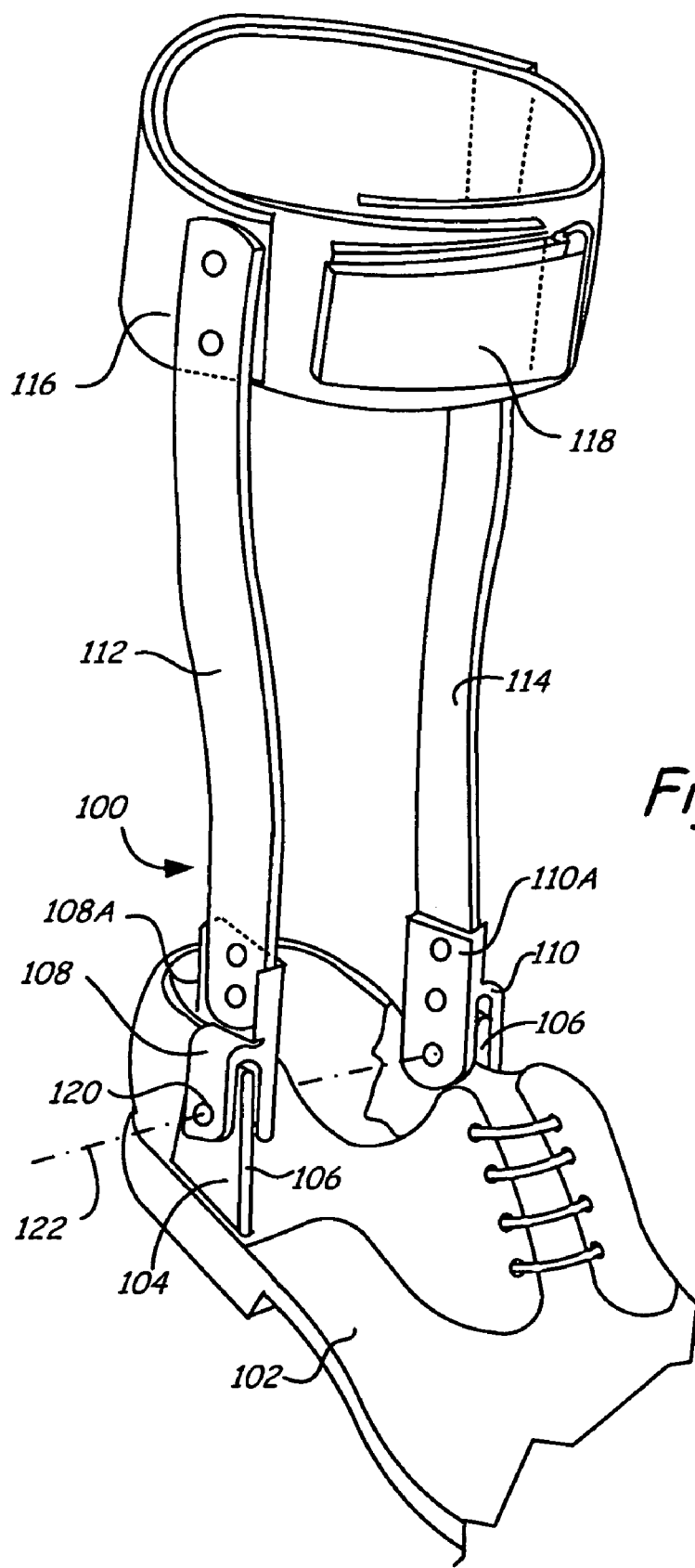
FIG. 8 is a perspective view of a modified form of an orthosis made of metal.
Figure 9:
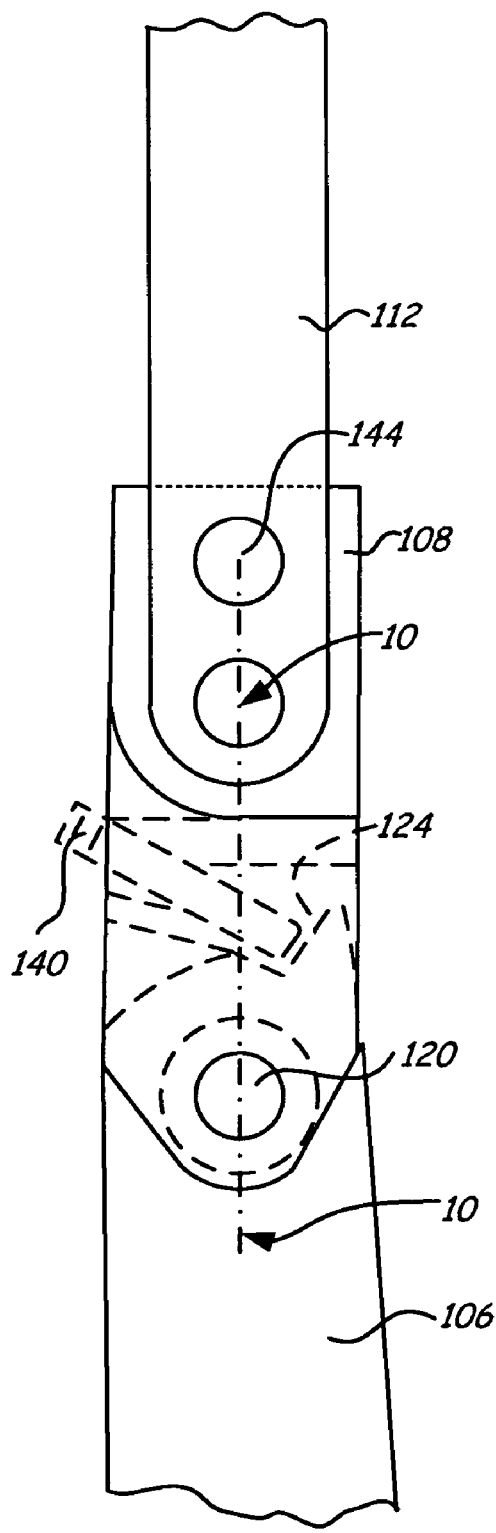
FIG. 9 is a side elevational view of one of the hinge joints of the orthosis of FIG. 8.
Figure 10:
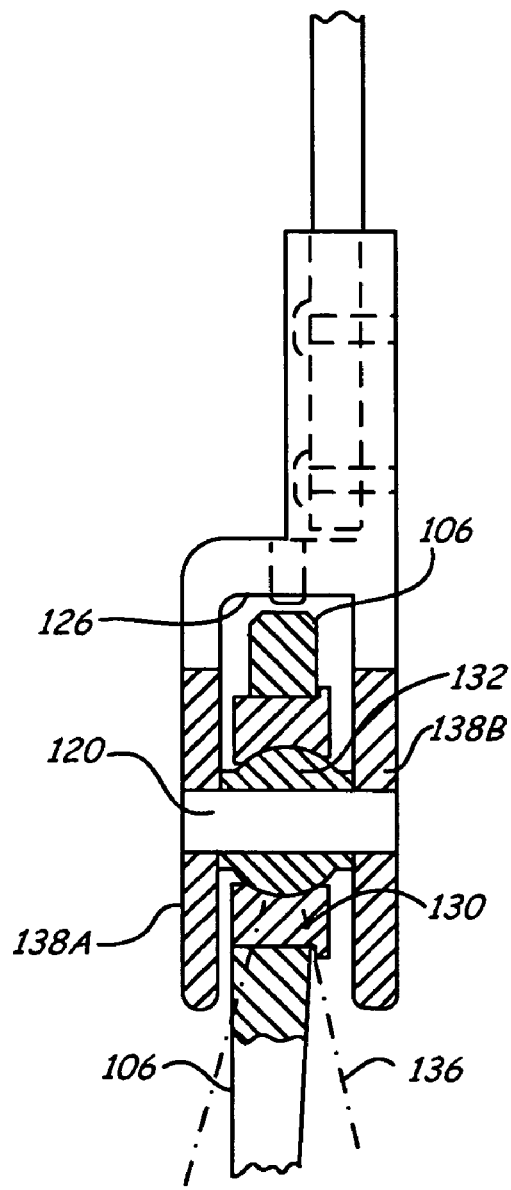
FIG. 10 is a part sectional view taken on line 10—10 in FIG. 9.

In FIG. 8, an orthosis indicated at 100 is made of metal, as was stated, and is adapted to be used in connection with a shoe 102. A stirrup 104 is supported underneath the sole of the shoe 102, in an accepted manner, and the stirrup 104 has upright extending side members 106, 106 that fit into devises 108 and 110 on opposite sides of the shoe. The strap 106 and the devises 108 and 110 are parts of joint components 108A and 110A that in this form of the invention are attached to support upright straps 112 and 114, respectively, on opposite sides of the orthosis. The straps 112 and 114 extend upwardly, and are mounted onto sides of an attachment cuff 116, in a known suitable manner, and the cuff 116 can be opened and closed for attaching and removing the orthosis. The cuff is held closed with a releasable fastener arrangement 118. The cuff goes around the leg of a wearer of the orthosis, with a foot in the shoe 102.

The orthosis is made so that the devises 108 and 110 comprising one part of each joint component are pivotally mounted on the respective sides straps 106, which are the second parts of each joint component with pivot pins 120, for movement about an axis 122.

The straps 106 both have an upper edge that is shown in dotted lines at 124, that is within the upper wall 126 of the clevis 108. The upper portion of each of the straps 106 has a spherical bearing race 130 mounted therein, to support a spherical bearing 132 that is the same as bearing 40. The bearing 132 of each joint component has a spherical outer surface so that the straps 106 can move angularly relative to the pivot pin and the respective clevis. The angular movement is represented in dotted lines at 136.

The spherical bearing 132 is retained between the side straps 138A and 138B of the respective clevis 108 and 110 and is retained in place so that there can be pivoting about the axis 122 as well as about axes perpendicular to axis 122. Thus, some misalignments of the joint components 108A and 110A can be accommodated between the two sides of the orthosis as previously explained.

A stop set screw 140 is threaded through a housing portion of each clevis, and in particular the upper wall 126, to engage an upper edge 124 of the straps 106 on each side to limit pivoting. The upper edge 124 can also be configured to abut against the under surface of the wall 126 for stopping in both directions.

The leg straps 112 and 114 can be attached to the brackets 108A and 110A, with suitable fasteners 144, as shown. The pivot pin 120 can be also made as desired, pivoting about the axis 122.

The pivoting joint components made of two parts joined with a spherical bearing can utilized for orthoses that are made of metal and have straps going up along the sides of the leg and are held in place with suitable cuffs or fasteners.

In the process of fabricating an orthosis for a particular individual, the stirrup 106 and straps 112 and 114 are bent to the proper dimensions and contours in stages. In a late stage the joint must be fastened in place to check over all alignment. At that point it is helpful to have the joint component held in its neutral mid-alignment position. Part of the invention is the use of a plug tightly fit into the joint filling the spaces between the stirrup ends, and the clevis. This insures that in the final hardware alignment the joint is not at or near the limit of its potential to accommodate misalignment.

An alternative way to achieve such assurance is to provide and use a rigid non-articulated "dummy" joint unit that is fastened into place during fabrication but then exchanged for the real joint as the final step.

Although the present invention has been described with reference to preferred embodiments, workers skilled in the art will recognize that changes may be made in form and detail without departing from the spirit and scope of the invention.

What is claimed is:

1. A joint component for an orthosis assembly for providing skeletal joint control of a limb, comprising:
    medial and lateral joint components for joining first and second orthotic sections forming the orthosis assembly, said medial and lateral joint components each having first and second parts hinged together, the first part of each of the joint components being attachable to the first orthotic section, and the second part of each joint component being attachable to the second orthotic section, the first and second parts of each of the joint components being connected through a spherical pivot that permits hinging along a first axis lying between the lateral and medial joint components, and being free for simultaneous pivoting about axes perpendicular to the first axis when attached to the first and second orthotic sections, the first part at least one joint component having a housing portion offset from the first axis, a screw threaded through a bore in the housing portion having an end extendable out of the housing portion and positioned to engage the second hinge part to adjustably stop pivoting of the hinge parts.

2. The joint component of claim 1, wherein the joint components have a range of motion about the perpendicular axes limited to a selected included angle.

3. The joint component of claim 1, wherein the joint components are constructed such that a first joint part has a clevis at an outer end thereof, and the second joint part has a spherical bearing that fits into the clevis and is pivotally secured thereto about the first pivot axis.

4. The joint component of claim 3, wherein the first and second joint component parts are coupled with overlapping flange and tongue members that join the spherical bearing between the two joint component parts.

5. The joint component of claim 3, wherein said spherical bearing comprises a sintered metal impregnated with a lubricant.

6. The joint component of claim 1, wherein the first part of each of the joint components comprises a tongue, a bearing race in the tongue for seating a spherical bearing, a bearing mounted in the bearing race, the bearing having a part spherical outer surface and a central bore, an overlapping flange member on the second of the parts that overlaps the bore, and a pivot pin extending through the overlapping flange member and the bore to pivotally mount the two parts of the joint component together about an axis of the bore of the central bearing.

7. A joint component for joining first and second orthotic sections, said joint component having first and second parts hinged together about a first axis, the first part having a portion attachable to a first orthotic section, and the second part having a portion attachable to a second orthotic section to join the orthotic sections for hinging movement, the first and second parts being connected through a spherical pivot that permits free hinging a selected amount about the first axis and that also permits free pivoting of the first and second parts about axes transverse to the first axis during use when the first and second parts are joined to the first and second orthotic sections, the first part comprising a tongue, the spherical pivot comprising a bearing race in the tongue for seating a spherical bearing and a spherical bearing mounted in the bearing race, the spherical bearing having a part spherical outer surface with a central bore, the second part having a clevis with side members that overlap the bore, and a pivot pin extending through the side members and the bore to pivotally mount the first and second parts of the joint component together.

8. The joint component of claim 7 wherein the parts have an adjustable range of motion about the transverse axes of up to a 24° included angle.

9. The joint component of claim 7 wherein the orthotic sections comprise molded plastic shells.

10. The joint component of claim 7 wherein the orthotic section comprise metal straps secured to the parts of the joint components.

* * * * *